US005476513A

United States Patent [19]
Brady et al.

[11] Patent Number: 5,476,513
[45] Date of Patent: Dec. 19, 1995

[54] INTRAOCULAR LENS

[75] Inventors: Daniel G. Brady, Mission Viejo; Christopher Doyle, Irvine; Bernard F. Grisoni, Aliso Viejo, all of Calif.

[73] Assignee: Allergan, Inc., Irvine, Calif.

[21] Appl. No.: 19,936

[22] Filed: Feb. 19, 1993

Related U.S. Application Data

[63] Continuation-in-part of Ser. No. 843,527, Feb. 28, 1992, Pat. No. 5,201,763.

[51] Int. Cl.$^6$ ............................................. A61F 2/16
[52] U.S. Cl. ............................................. 623/6; 351/160 R
[58] Field of Search ........................... 623/6; 606/107; 351/160 R

[56] References Cited

U.S. PATENT DOCUMENTS

| | | |
|---|---|---|
| 3,284,406 | 11/1966 | Nelson . |
| 3,341,490 | 9/1967 | Burdick . |
| 3,457,214 | 7/1969 | Modic . |
| 3,992,355 | 11/1976 | Itoh et al. . |
| 3,996,187 | 12/1976 | Travnicek . |

(List continued on next page.)

FOREIGN PATENT DOCUMENTS

| | | | |
|---|---|---|---|
| 1273144 | 8/1990 | Canada . | |
| 0110537 | 6/1984 | European Pat. Off. . | |
| 0202049 | 11/1986 | European Pat. Off. . | |
| 0226400 | 6/1987 | European Pat. Off. . | |
| 0269288 | 6/1988 | European Pat. Off. . | |
| 0335312 | 10/1989 | European Pat. Off. . | |
| 0556040 | 8/1993 | European Pat. Off. . | |
| 2124500 | 2/1984 | United Kingdom | 623/6 |
| 2181355 | 4/1987 | United Kingdom | 623/6 |

OTHER PUBLICATIONS

Vol. 13, No. 79 (C-571) (3427) Feb. 22, 1989 Abstract from Japan (63-267351).
Saam, Formation of Linear Siloxane Polymers, 1990 American Chemical Society, pp. 71-89.
Grigoras et al, Conformational Analysis of Substituted Polysiloxane polymers, 1990 American Chemical Society, pp. 125-144.
Rasoul et al, Thermal and Rheological Properties of Alkyl-Substituted Polysiloxanes, 1990 American Chemical Society, pp. 91-96.
Zaph et al, Synthesis and Properties of New UV-Curable Silicones With High Refractive Index, Polymeric Prints 30(2), pp. 107 (1989).
Boutevin et al, Synthesis of Fluorinated Polysiloxanes, 8. Properties at Low and High Temperatures of Polysiloxanes with Fluronated Grafts, Macromolecules, vol. 24, (3), pp. 629-632 (Feb. 4, 1991).
Grigoras, Substituted Polysiloxane Polymers: Conformation of the Pendant Groups, Polymeric Prints, 31(1), 697(1990).
Fish et al, Ring Opening Polymerization of Cylotetrasiloxanes with Large Substituents, pp. 36-37, Polymer Reprints, 31(1), Apr. 1990.
Christ et al, "Evaluation of the chemical, optical, and mechanical properties of elastomeric intraocular lens materials and their significance", J. Cataract Refract Surg-vol. 15, Mar. 1989, pp. 176-184.
"Acrylens A Technical Evaluation of Foldable Intraocular Lenses", Ioptex Research Inc, copyright 1990.

*Primary Examiner*—Mary Beth O. Jones
*Attorney, Agent, or Firm*—Frank J. Uxa

[57] ABSTRACT

An intraocular lens for implantation in an eye comprising an optic configured so that the optic can be deformed to permit the intraocular lens to be passed through an incision into the eye. A peripheral zone circumscribes the optical zone of the optic and one or more fixation members coupled to the peripheral zone and extending outwardly from the peripheral zone to retain the optic in the eye are provided. In one embodiment the fixation member or members are located so that the optical zone is free of such member or members. The peripheral zone preferably has a maximum axial thickness which is larger than the maximum axial thickness of the periphery of the optical zone.

24 Claims, 3 Drawing Sheets

U.S. PATENT DOCUMENTS

| | | | |
|---|---|---|---|
| 3,996,189 | 12/1976 | Travnicek. | |
| 3,996,935 | 12/1976 | Banko | 604/22 |
| 4,189,546 | 2/1980 | Deichert et al. | 623/6 X |
| 4,380,643 | 4/1983 | Yoshida et al. . | |
| 4,418,165 | 11/1983 | Polmanteer et al. . | |
| 4,424,597 | 1/1984 | Schlegel | 623/6 |
| 4,535,141 | 8/1985 | Kroupa . | |
| 4,573,998 | 3/1986 | Mazzocco . | |
| 4,605,409 | 8/1986 | Kelman | 623/6 |
| 4,615,702 | 10/1986 | Koziol et al. . | |
| 4,624,670 | 11/1986 | Bechert, II | 623/6 |
| 4,647,282 | 3/1987 | Fedorov et al. . | |
| 4,661,108 | 4/1987 | Grendahl et al. | 623/6 |
| 4,673,406 | 6/1987 | Schegel | 623/6 |
| 4,702,244 | 10/1987 | Mazzocco | 623/6 |
| 4,704,124 | 11/1987 | Shearing | 623/6 |
| 4,715,373 | 12/1987 | Mazzocco et al. | 623/6 X |
| 4,737,558 | 4/1988 | Falcetta et al. . | |
| 4,769,035 | 9/1988 | Kelman | 623/6 |
| 4,781,717 | 11/1988 | Grendahl | 623/6 |
| 4,785,047 | 11/1988 | Jensen . | |
| 4,790,846 | 12/1988 | Christ et al. . | |
| 4,834,754 | 5/1989 | Shearing | 623/6 |
| 4,868,251 | 9/1989 | Reich et al. . | |
| 4,878,912 | 11/1989 | Castleman . | |
| 4,882,398 | 11/1989 | Mbah . | |
| 4,911,714 | 3/1990 | Poley . | |
| 5,041,134 | 8/1991 | O'Donnell | 623/6 |
| 5,180,390 | 1/1993 | Drews | 623/6 |
| 5,201,763 | 4/1993 | Brady et al. | 623/6 |
| 5,203,789 | 4/1993 | McDonald | 623/6 |
| 5,203,790 | 4/1993 | McDonald | 623/6 |
| 5,236,970 | 8/1993 | Christ et al. | 623/6 X |

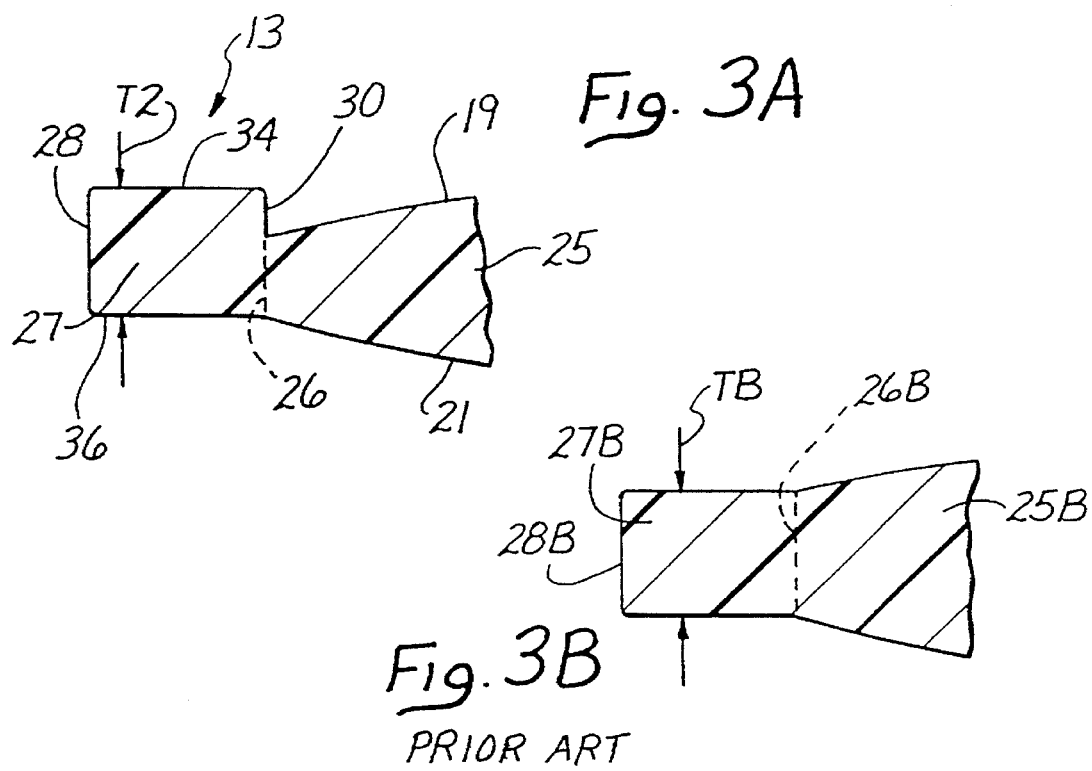
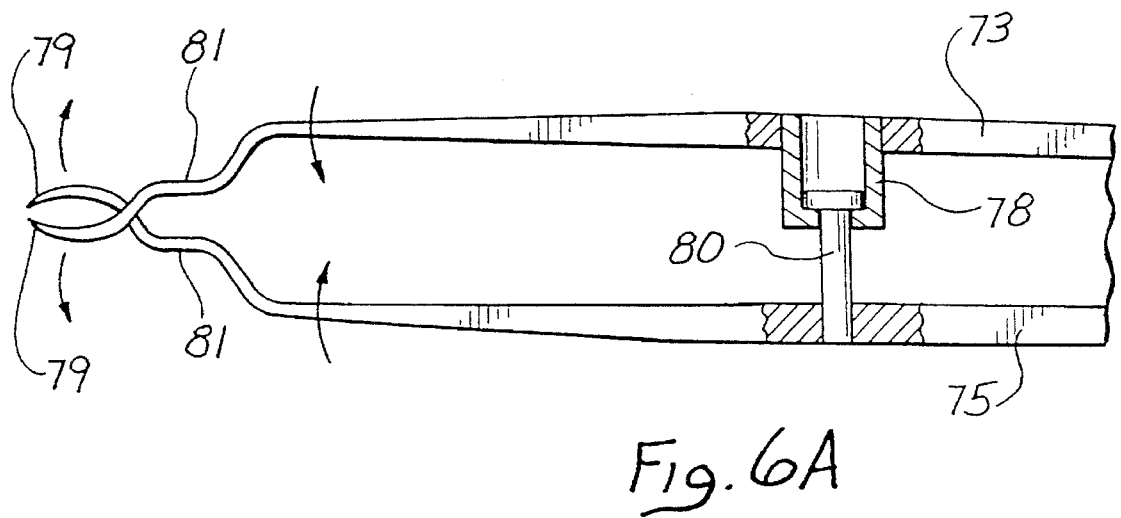

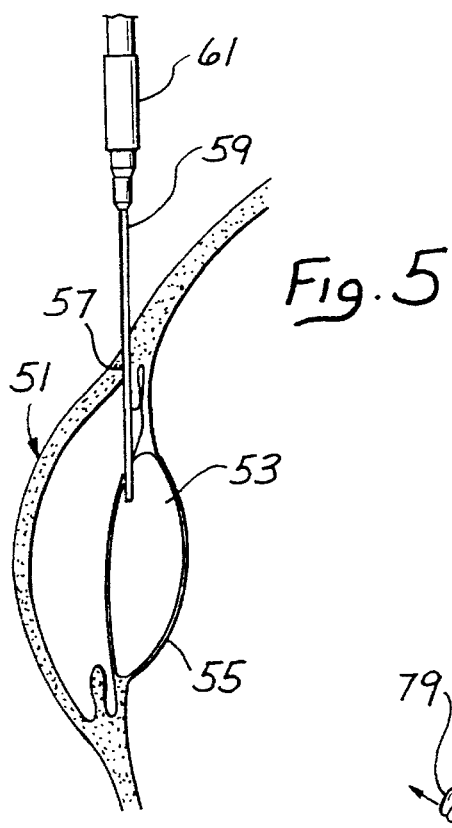
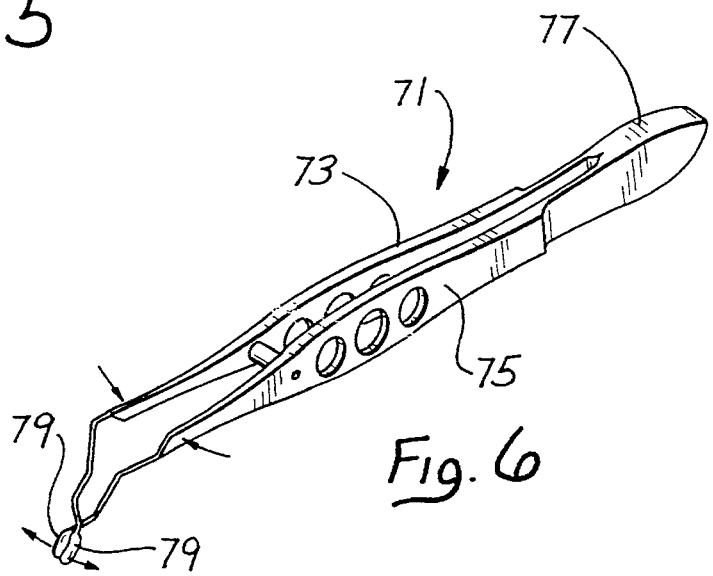
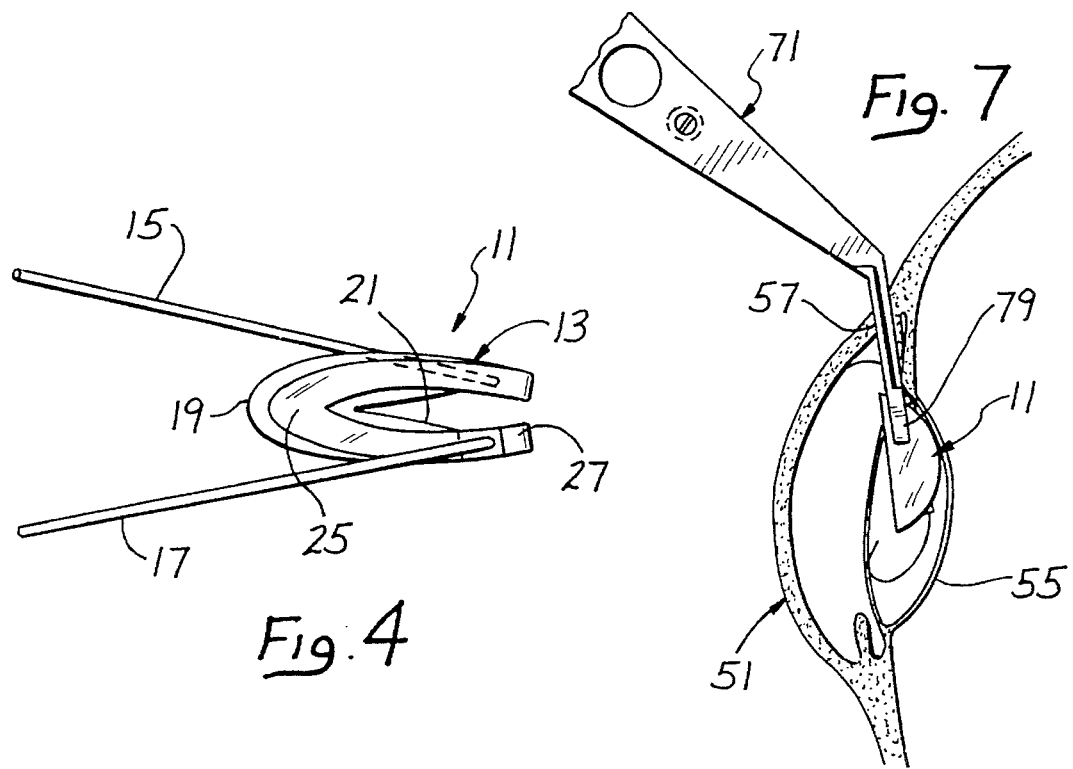

INTRAOCULAR LENS

RELATED APPLICATION

This application is a continuation-in-part of application Ser. No. 843,527 filed Feb. 28, 1992, now U.S. Pat. No. 5,201,763. This prior application is incorporated in its entirety by reference herein.

FIELD OF THE INVENTION

This invention relates to an intraocular lens (IOL) and more particularly to an IOL with a deformable optic which enables the IOL to be passed through an incision, for example, a scleral tunnel incision having an end-to-end dimension no larger than about 3.2 mm or no larger than about 2.8 mm, into the eye. This end-to-end dimension of the incision, that is the shortest distance along the surface being cut from one end of the incision to the other end of the incision, is hereinafter referred to as the dimension of the incision.

BACKGROUND OF THE INVENTION

When the natural lens of the human eye becomes impaired through, for example, cataracts or injury, it is common practice to replace the natural lens with an IOL. One way to accomplish this is to form a relatively long incision in the eye and remove the natural lens in one piece. However, presently a much more common way to accomplish this is to form a shorter incision in the eye and insert a probe or a phaco tip of a phacoemulsification instrument through the incision into the eye to break up the natural lens using ultrasonic energy. The lens fragments are then aspirated from the eye through the relatively short phaco incision and the phaco tip is removed.

The dimension of the incision, which is commonly referred to as a phaco incision, in the eye through which the phaco tip is inserted is typically no larger than about 2.8 mm or about 3.2 mm so that the phaco tip will fit somewhat snugly through the incision. It is generally recognized that the larger the lens-removal incision, the greater the trauma to the eye and the longer the patient recovery time. Other complications may also be caused by a large incision such as the need to remove the lens in one piece. About 70 percent of the lens-removal processes currently use phacoemulsification techniques. Of course, with only a small incision being needed for phacoemulsification lens extraction, it is desirable that IOL's be available and used that can be inserted through the small phaco incisions.

A typical IOL includes an optic, usually having a diameter of about 6 mm, and fixation members coupled to (or formed with) the optic to fix the optic within the eye in the region of the extracted lens. IOL's are of two basic types, those having a hard or rigid optic formed, for example, of polymethylmethacrylate (PMMA) and those having a deformable optic which is constructed of a deformable material such as silicone, hydrogel, or an acrylic. If a hard IOL is used, the small phaco incision must be enlarged to approximately the diameter of the hard optic, in order to permit the hard optic to be inserted through the incision and much of the advantage of phacoemulsification lens extraction is thereby obviously lost.

There are two known classes of prior art IOL's which can be deformed (e.g., folded or rolled) to pass through a scleral tunnel incision having a dimension of about 3.2 mm. A scleral tunnel incision is a single incision in the sclera without any additional incision which crosses or intersects the single incision. The first of these IOL's has an acrylic optic with a refractive index of about 1.47 or greater. The acrylic IOL's cover a full diopter range of about $12d$ to about $24d$, but do not have as high an elongation as is desired for IOL insertion through a small phaco incision. Elongation is defined as $(L_d/L_u)$ times 100 where $L_d$ is the maximum change in length from the unstressed condition to the breaking point and $L_u$ is the unstressed length. A high elongation is desired so that the optic can be caused to resiliently stretch and flow to assume a small cross sectional configuration for passage through a small phaco incision. For example, a currently known acrylic optic may have an elongation of only about 150 percent.

The second of these classes of IOL's has a silicone based optic. In one known silicone based optic the refractive index is only about 1,408. Accordingly, it is necessary to have a relatively large maximum cross sectional area of about 5.1 square millimeters in order to provide an IOL of only 12 diopter power. Although higher diopter powers can be constructed with this silicone based material, the higher powers require a correspondingly greater maximum cross sectional area with the result that they will not ordinarily pass through a scleral tunnel incision having a dimension of only about 2.8 or about 3.2 mm in the eye. More specifically, the present inventors understand that it is highly unlikely that this type of silicone IOL is implantable, using a stainless steel folding forceps-type inserter, through a 3.2 mm scleral tunnel incision in powers over $14d$ and that in powers over $15d$ implantation through a 3.2 mm scleral tunnel incision into the eye is essentially not possible. Implantation of an IOL of this type having a power of $20d$ or greater is not possible.

A second kind of known silicone based optic is disclosed in Fedorov et al U.S. Pat. No. 4,647,282. One of the silicone based materials disclosed in this patent is said to have a refractive index of 1.480. However, this silicone based material has a percentage of elongation of only 130 percent, and the patent lacks, among other things, specific geometrical teachings as to how the optic is to be constructed.

A third kind of known silicone based optic is disclosed in U.S. Pat. No. 5,236,970 and entitled OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES. At present, a known 16 diopter power optic of this material has a maximum cross sectional area of about 5.3 sq. mm.

Another important consideration in producing small deformable IOL's is the placement of the fixation members or haptics, used to assist in retaining the optic in the eye, relative to the optic. Because of strength, molding and other material concerns, it has heretofore been considered necessary to secure the proximal end of the fixation members in the optical zone of the optic of such IOL's, for example, when the IOL is constructed so as to be deformed and placed in the eye through a small incision. This construction has at least one disadvantage, a portion of each of the fixation members exists in the optical field defined by the optic and, therefore, can interfere with the patient's vision. This problem is exacerbated by the current trend to smaller and smaller IOL optics. It would be advantageous to provide an IOL including one or more fixation members, for example, of the filament type, in which the optical zone of the optic is completely free of the fixation members.

SUMMARY OF THE INVENTION

New IOL's have been discovered. In one embodiment, the IOL's of the present invention include optics with optical zones having a periphery with a reduced thickness (parallel to the optical axis of the optic) relative to prior art lenses of the same type. This reduced thickness allows the optic to be deformed, for example, rolled or folded, for insertion in the eye through a very small incision, preferably having a dimension on the order of about 3.2 or even about 2.8 mm. Such reduced thickness is achieved without any substantial detriment, for example, to the optical properties and power of the optical zone of the optic. Consequently, the phaco incision, which is commonly used for the phaco tip, need not be enlarged in order to permit the IOL to be implanted. The fixation member or members of the present IOL's are preferably secured to the peripheral zone circumscribing the optic so as not to interfere with the optic. In short, the present invention provides very effective and useful small incision IOL's the optics of which have optical zones with reduced peripheral thickness and/or are free of fixation member interference.

When an IOL of this invention is implanted in the eye, the optic has sufficient rigidity to be substantially free of optical distortion resulting from force from the eye acting on the IOL. The optic is preferably of sufficient size and/or is suitably structured to reduce, or even substantially prevent, the glare that would result if the dimensions of the optic were so small that light could interact with the periphery of the optic to cause glare. In one embodiment, the optical zone of the optic is constructed of optically clear material, and the peripheral zone, which circumscribes the optical zone, is structured to provide reduced glare relative to a substantially identical IOL with the peripheral zone made from the same optically clear material. For example, the peripheral zone of the optic can be at least partially roughened. Such toughening acts to reduce the glare exhibited by the implanted optic relative to a substantially identical optic without a roughened peripheral zone.

The optic preferably has an elongation of at least about 160 percent or about 200 percent. Preferably, the elongation of the optic is at least about 260 percent.

This invention is applicable to a very high percentage of the diopter powers currently being employed in IOL's. The invention is specifically applicable to deformable optics with optical zones having from about 12 to about 24 diopter power, and this range of diopter powers is believed to be prescribed for about 95 percent of all IOL recipients. The features of this invention are applicable, for example, to an optic with optical zones having at least about 20 diopter power, and this is a higher power than the diopter power of known prior art silicone IOL's that were implantable through a 3.2 mm scleral tunnel incision.

This invention is based, in part, upon the recognition by the present inventors that the maximum cross sectional area of the optic is a primary controlling factor in determining the dimension of the incision required for insertion of the deformable optic through the incision. More specifically, for insertion through scleral tunnel incisions having a dimension of no greater than about 3.2 mm or about 3.0 mm, the maximum cross sectional area of the optic should be no greater than about 5.8 square mm.

In addition, the present inventors have discovered that the peripheral thickness of the optical zone can be reduced without substantially detrimentally effecting the optical properties of the optical zone. More specifically, the cross-sectional area of the optic can be reduced (and maintain the same optical power) by forming the optic so that the peripheral zone has a maximum axial thickness (parallel to the optical axis) which is larger than the maximum axial thickness of the periphery (which may be imaginary) of the optical zone. Of course, in accordance with the present invention, the optical power of the optical zone can be increased while maintaining the cross-sectional area of the optic constant. The reduction in optic cross-sectional area or the increase in optical power is relative to a substantially identical IOL in which the peripheral zone has a maximum axial thickness which is the same as the maximum axial thickness of the periphery of the optical zone. In the present invention, the peripheral zone is maintained at a sufficient thickness so as to allow the fixation member or members of the IOL to be firmly secured to the optic.

The optic of this invention has an optical axis, anterior and posterior faces, and the curvature of one or both of these faces determines the corrective or diopter power of the optic. In order to keep the maximum cross sectional area at or below the desired maximum, it is desirable to minimize the convex curvature of the face or faces which provide the correction. To obtain the necessary correction without undue convex curvature which would thicken the optic, it is preferred, but not essential, to employ an optic having an index of refraction of at least about 1.40 with an index of refraction of at least about 1.46 being preferred. An index of refraction less than 1.40 tends to limit the diopter correction that is obtainable or require other trade offs that may be undesirable.

It is also important that the optic not be made so thin that, when implanted and subjected to the usual forces from the eye, it buckles or deforms and thereby introduces optical distortion. The relatively thick peripheral zone of the present IOL's inhibits, to some extent, such buckling or deforming. The peripheral zone preferably forms, in effect, a frame which assists in strengthening the optic against unwanted deformation after implantation. The peripheral zone preferably includes buttresses for use in attaching the fixation members to the optic and for lending support to the optic. For one preferred construction, the thickness of the optic along the optical axis is no less than about 0.65 mm or about 0.68 mm to about 0.79 mm in order to guard against the optical distortion that would result from mechanical deformation of the optic of the implanted IOL.

The optic should also be constructed so as to reduce or even substantially prevent glare. To accomplish this, the optic, including the optical zone and peripheral zone, should preferably have sufficient radial dimensions to cover the optical zone within the eye to assure that light rays do not interact with the edges of the optic sufficiently to cause glare. In a preferred construction, the optic is circular and has a diameter of at least about 6 mm, although glare can be substantially prevented by an optic having smaller diameters down to about 5 mm. All or a portion of the peripheral zone of the optic may be structured, for example, have at least a portion of its surface toughened, to provide reduced glare relative to a substantially identical intraocular lens with the peripheral zone made from an optically clear material.

Fixation members are used to fix the optic within the eye. Another important consideration is constructing the optic in a way that enables the obtaining of a strong attachment between the fixation members and the optic. The peripheral zone is not used for focusing of light on the retina, but is used for receiving attachment regions of the fixation members for attaching the fixation members to the optic. The central optical zone is used for focusing light on the retina and providing the desired correction. The peripheral zone and fixation member or members are preferably constructed so that the optical zone of the optic is completely free of the fixation member or members. In a particularly useful construction, the proximal end portion of one or more of the fixation members, for example, that portion of the fixation member located in the optic, extends in a direction which is generally tangential to the optic.

Because the peripheral zone adds to the maximum cross sectional area of the optic and does not effectively contribute to the optical properties, for example, the optical power, of the IOL, it is desirable to reduce the axial cross sectional area of the peripheral zone to a minimum. On the other hand, a certain thickness, i.e. axial dimension, of the peripheral zone is needed in order to form a strong attachment with the fixation members and/or to provide advantageous strength to the optic. In a preferred construction, the thickness of the peripheral zone in the axial direction is no less than about 0.305 mm with a thickness no less than about 0.381 mm being more preferred.

Other properties of interest of the optic include hardness and tensile strength. Preferably, the hardness of the optic is at least about 38 Shore A so that compressive forces exerted on the optic by the tool used for implanting the IOL is less likely to permanently scratch or mark the IOL. In addition, the optic preferably has a tensile strength of no greater than about 1000 psi because tensile strengths greater than this make the optic more difficult to elongate during insertion. The tensile strength should preferably be greater than about 600 psi in order to prevent mechanical distortion of the optic when the fixation members are resiliently urged radially inwardly.

The optics of the present IOL's may be constructed of any suitable material or combination of materials. Such materials include, for example, silicone based materials (polymeric materials), acrylic polymeric materials, hydrogel-forming polymers and the like and mixtures thereof. Certain silicone based materials possess a number of properties which adapt them for use as the optic material. Preferably the silicone based materials are substantially free of acrylates. Preferred silicone based materials are described in U.S. Pat. No. 5,236,970 referred to above and entitled OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES. This application is incorporated in its entirety by reference herein.

The fixation members can be of various configurations and material. For example, the fixation members may be constructed of PMMA or polypropylene. To more desirably apply the forces on the optic caused by the eye after implantation, each of the fixation members is preferably in the form of a C-shaped elongated resilient member. Preferably the fixation members are coupled to the optic at generally diametrically opposed locations.

The invention, together with additional features and advantages thereof may best be understood by reference to the following description taken in connection with the accompanying illustrative drawings.

BRIEF DESCRIPTION OF THE DRAWINGS

FIG. 3A is a partial sectional view of the IOL of FIG. 1.

FIG. 3B is a partial sectional view of a comparative IOL.

FIG. 4 is an elevational view illustrating the IOL in a folded condition for insertion into the eye.

FIG. 5 is a perspective view illustrating the use of a phacoemulsification instrument to remove the natural lens of an eye.

FIG. 6 is a perspective view illustrating a representative form of insertion tool utilized for deforming the IOL and inserting it through an incision into the eye.

FIG. 6A is a fragmentary plan view partially in section showing the distal portion of the insertion tool.

FIG. 7 is a perspective view illustrating insertion of the IOL through the unlengthened phaco incision.

DESCRIPTION OF THE PREFERRED EMBODIMENT

Figure 2:
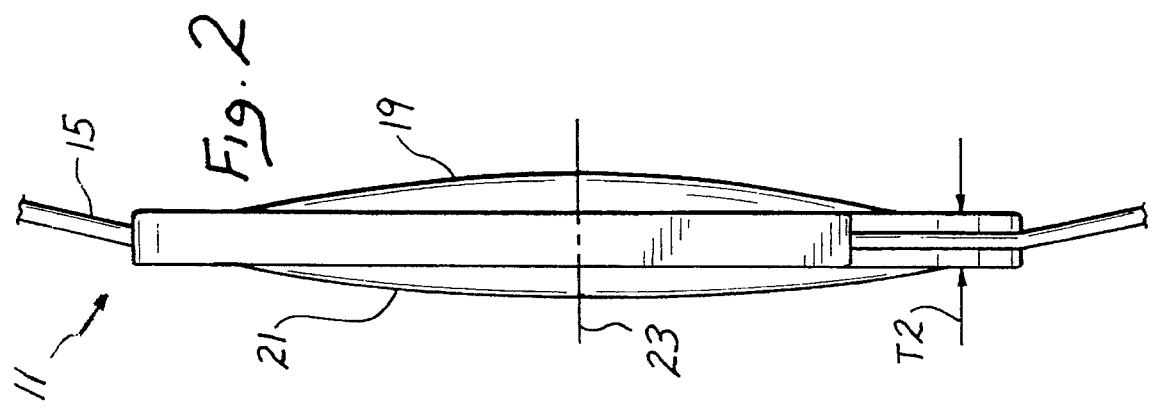
FIG. 2 is a side elevational view of the IOL of FIG. 1.
Figure 1:
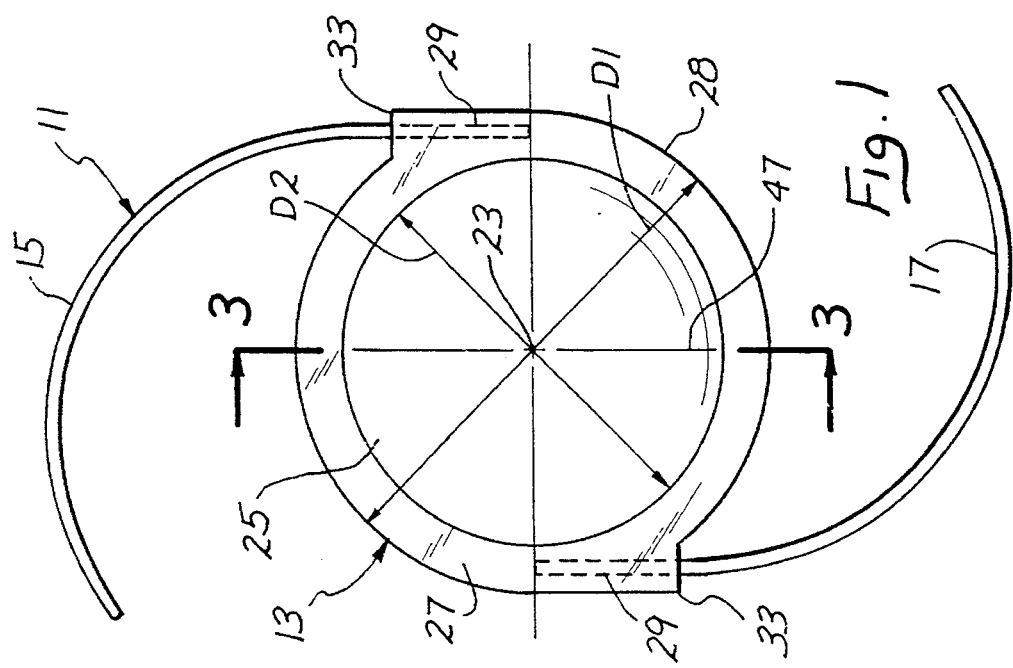
FIG. 1 is a plan view partially in section of a three piece IOL constructed in accordance with the teachings of this invention.

FIGS. 1 and 2 show an IOL 11 which generally includes an optic 13 and identical fixation members 15 and 17. The optic 13 is resilient and deformable and preferably constructed (as by molding) of resilient deformable silicone based material having a refractive index of about 1.46, an elongation of about 260 percent, a tensile strength up to about 1000 psi and a Shore A hardness of about 38. Particularly useful silicone based materials are disclosed more fully below. Although various configurations may be employed for the optic 13, in the illustrated embodiment, the optic 13 is biconvex, is circular in plan and has an outer diameter D1 of about 6 mm.

The optic 13 includes an optical zone 25 which has an anterior face 19 and posterior face 21. As illustrated, the faces 19 and 21 are both convex, and this is preferred. However, other configurations, Such as plano-convex, which will yield the desired diopter power range, could alternatively be employed.

The various geometrical parameters for the optic 13 have been especially developed to enable the IOL 13 to be folded to a sufficiently small size to enable implantation through a scleral tunnel incision having a dimension of no more than about 3.0 mm or about 2.8 mm, and this is possible for optics having a range of diopter powers from about 12 to about 24. The optic 13 has an optical axis 23 and the thickness T1 of the optic 13 along the optical axis, i.e. the center thickness, is no less than about 0.65 mm, for example, about 0.68 mm to about 0.79 mm. The optic 13 has central optical zone 25 with a diameter D2 and an imaginary periphery 26, an annular peripheral zone 27 circumscribing the optical zone and a periphery 28. The thickness T2 of the peripheral zone 27 in the axial direction, i.e. as viewed in FIG. 2, is preferably no less than about 0.381 mm although thickness as small as about 0.305 mm can be employed. The thickness of the periphery 26 of the central optical zone 25 is less than the thickness T2 of peripheral zone 27. The optical zone 25 is circular as viewed in plan (FIG. 1) and forms the lens portion or operative vision correction portion of the optic 13. The zones 25 and 27 are of integral, one-piece construction.

Figure 3:
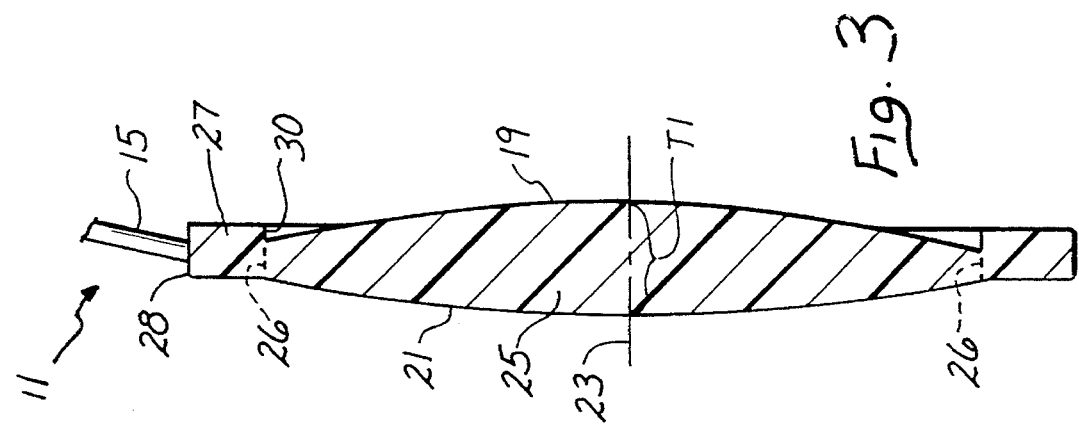
FIG. 3 is a sectional view taken generally along line 3—3 of FIG. 1.

The optic 13 has a maximum cross sectional area which, in the embodiment illustrated, is the cross sectional area of the optic along a diameter. The maximum cross sectional area of the optic 13 is shown in cross section in FIG. 3 and is preferably no greater than about 5.8 square mm.

The peripheral zone 27 is a non-optical zone and does not form a part of the lens of the optic 13. The functions of the peripheral zone 27 include strengthening the optical zone 25 against deformation when implanted, mounting or attaching the fixation members 15 and 17 to the optic 13 and adding to the diameter of the optic 13 to reduce the likelihood of light interacting with the periphery 28 of the optic to cause glare after implantation. In one embodiment, the external surfaces, for example, the periphery 28 and inwardly facing wall 30, of peripheral zone 27 are roughened to reduce or prevent glare. In addition, the corners and edges of peripheral zone 27 are preferably rounded rather than being sharp (or formed by intersecting straight surfaces) so as to reduce edge glare.

FIGS. 3A and 3B illustrate in detail the "reduced thickness" feature of the present invention. In FIG. 3B, the thickness TB of the peripheral zone 27B is equal to the thickness of the periphery 26B of optical zone 25B of optic 13B. In contrast, the thickness T2 of the peripheral zone 27 is greater than the thickness of the periphery 26 of optical zone 25 of optic 13. This reduced peripheral thickness of optical zone 25 results in optic 13 having a reduced cross-sectional area relative to optic 13B. It should be noted that in this illustration the overall radial dimensions of optics 13 and 13B are the same, the thicknesses T2 and TB are the same, the optical powers of optical zones 25 and 25B are the same and the overall configuration of peripheral zones 27 and 27B are the same.

The drawings illustrate an embodiment in which only the anterior face 19 of optical zone 25 terminates a distance (measured by the length of inwardly facing wall 30) away from the top surface 34 of peripheral zone 27. However, other embodiments are effective and are included in the scope of the present invention. For example, only posterior face 21 can terminate a distance away from the bottom surface 36 of peripheral zone; or anterior face 19 can terminate a distance away from the top surface 34 and posterior face 21 can terminate a distance away from the bottom surface 36. The peripheral zone 27 is partially defined by periphery 26, and a finite portion of the peripheral zone may have a thickness equal to the thickness of the optical zone 25 at its periphery. Periphery 26 of optical zone 25 should have sufficient thickness to prevent peripheral zone 27 separating or being torn away from optical zone 25, for example, under normal lens insertion conditions and under normal use conditions in the eye.

Although the fixation members 15 and 17 may be of various different constructions and materials, in this embodiment each of them is in the form of a generally C-shaped resilient fiber or strand of PMMA. Each of the fixation members 15 and 17 has a proximal end portion which is located in peripheral zone 27 and extends in a direction generally tangential to the optic 13. The material of the peripheral zone 27 completely surrounds the proximal portions 29 and strongly attaches the fixation members to the optic 13 at diametrically opposed locations. The central optical zone 25 is completely free of, and unobstructed by, the fixation members 15 and 17.

The IOL 11 can be made using an injection molding technique, and this as well as the use of the attachment loops 31, is described in Christ et al U.S. Pat. No. 4,790,846 which is incorporated by reference herein. Of course, various different techniques and constructions can be employed for providing some sort of fixation means for fixing the optic 13 in the eye, and the construction shown is merely illustrative.

The peripheral zone 27 preferably includes radial projections or buttresses 33 which receive a length of the attachment regions 29, respectively. The buttresses 33 aid the attachment of the fixation members 15 and 17 to the peripheral zone 27 and strengthen the optical zone 25 against deformation of the type that would create optical distortion in the eye.

The features of this invention typically enable the manufacture of a set of IOL's which are implantable through a scleral tunnel incision having a dimension of no more than about 3.0 mm or about 2.8 mm and which have from about 12 to about 24 diopter power. One preferred way of obtaining the desired features of this invention is to utilize a 6 mm diameter (D1) optic of silicone based material or a material having a refractive index of at least 1.40, an elongation of at least about 160 percent and the parameters set forth in the table below.

| Positive Diopter Power | Maximum Peripheral Zone 27 Axial Thickness | Optical Zone 25 Diameter | Periphery 26 Thickness |
|---|---|---|---|
| 12 to 14.5 | .457 mm | 5 mm | .355 mm |
| 15 to 18.5 | .381 mm | 5 mm | .304 mm |
| 19 to 21.5 | .381 mm | 5 mm | .254 mm |
| 22 to 24 | .381 mm | 5 mm | .203 mm |

FIG. 4 illustrates, by way of example, one way that the IOL 11 can be folded for insertion into the eye. In FIG. 4, the optic 13 is folded in half generally about a diameter, and the fold line may be generally along a reference line 47 shown in FIG. 1, although this is purely illustrative. The left half of the optic 13 shown in FIG. 1 is folded under the right half of the optic to provide the folded condition shown in FIG. 4. The fold can be along any desired diameter so as to place the fixation member 15 and 17 in the desired position for insertion. The fixation members 15 and 17 are sufficiently flexible so as not to impede insertion through the incision.

FIG. 5 schematically shows a human eye 51 which includes a natural lens 53 in the capsular bag 55. In order to remove the natural lens 53, a phaco incision 57 in the form of a scleral tunnel incision is formed in the eye as shown by way of example in FIG. 5 and a phaco tip 59 of a conventional phacoemulsification instrument 61 is inserted through the incision into the region of the eye containing the natural lens 53. The incision 57 is ordinarily no more than about 2.8 mm in dimension and the tissue of the eye typically fairly snugly surrounds the phaco tip 59. Ultrasonic energy provided by the instrument 61 breaks up the natural lens 53 and the lens fragments are aspirated from the capsular bag 55 using sub-atmospheric pressure applied through the phaco tip 59. After satisfactory removal of the natural lens 53, the phaco tip 59 is withdrawn from the eye 51 through the incision 57.

The next step is to insert the IOL 11 through the incision 57 without increasing the dimension of the incision. To accomplish this, the IOL 11 must be appropriately deformed so that the 6 mm diameter optic 13 can fit through a scleral tunnel incision having a dimension of no more than about 2.8 mm. This can be accomplished, by folding of the IOL 11 as shown by way of example in FIG. 4. The folding of the IOL 11 and its insertion through the incision 57 is preferably carried out with an appropriate insertion tool.

Various different insertion tools as are known to surgeons in the phacoemulsification and IOL implantation art such as the McDonald inserter, the Fine inserter, the McPherson forceps or the Tying forceps can be employed. FIG. 6 shows a conventional McDonald inserter 71 which includes resilient metal arms 73 and 75 joined together at a proximal end portion 77 so that the arms are resiliently urged away from each other. The arms 73 and 75 terminate in tips 79, respectively which are normally held in a closed position in which they are almost in contact with each other by the biasing force acting on the arms. A flanged sleeve 78 and a flanged pin 80 coupled to the arms 73 and 75 respectively form a stop which limits separation of the arms and prevents hard contact of the tips 79. Although the arms 73 and 75 are biased away from each other, the same biasing force urges the tips 79 toward each other by virtue of cross over sections 81 of the arms shown in FIG. 6A. The tips 79 and the cross over sections 81 are relatively rigid but of sufficiently small dimensions to pass through the incision 57 without lengthening of that incision.

The IOL 11 can be folded as shown in FIG. 4 and grasped between the tips 79. The IOL 11 can then be inserted through the incision 57 into the eye as shown schematically in FIG. 7 without enlarging the incision 57. The implantation procedure may be essentially the same as known procedures. Once implanted, the resilient, deformable optic 13 returns to its normal or undeformed condition and the fixation members 15 and 17 fix the IOL 11 in the eye in the usual manner.

Particularly useful silicone based materials are reinforced elastomeric compositions having the chemical composition of a cross-linked copolymer including about 12 to about 18 mol percent of aryl substituted siloxane units of the formula $R_4R_5$-SiO where the aryl substituents ($R_4$ and $R_5$ groups) can be can be independently selected from phenyl groups, mono- lower alkyl substituted phenyl groups, and di- lower alkyl substituted phenyl groups. Preferably, both aryl groups are simple phenyl, and the resulting diphenyl siloxane unit is present in the copolymer in an amount of about 14 to about 16 mol percent.

The copolymer is end blocked with trisubstituted (monofunctional) siloxane units. At least one substituent of the end blocking group contains an olefinic bond. Thus, the general formula of the end blocking group incorporated in the copolymer is $R_1R_2R_3SiO_{0.5}$ where the nature of the $R_1$ and $R_2$ is not critical, and they may be independently selected from, for example, alkyl, aryl, substituted alkyl and substituted aryl groups. $R_3$ contains an olefinic bond. $R_3$ is preferably an alkenyl group, more preferably a vinyl group. In a preferred embodiment, the end blocking group is a dimethyl, vinyl siloxane unit. The role of the olefinic (vinyl) group is to enable curing or cross-linking of the polymer, and preferably covalently linking certain ultraviolet light absorbing compounds to the cross-linked copolymer matrix.

The balance of the siloxane building blocks of the copolymer is preferably dialkyl siloxane units wherein the two alkyl substituents are either ethyl or methyl. In other words, the general formula of the balance of the siloxane building blocks of the copolymer is preferably $R_6R_7$-SiO where the $R_6$ and $R_7$ groups are independently selected from methyl and ethyl. Preferably both $R_6$ and $R_7$ groups are methyl.

The copolymer may have a degree of polymerization (dp) of about 100 to about 2000, although a degree of polymerization of about 250 is preferred, particularly when the $R_4$ and $R_5$ groups are phenyl and the $R_6$ and $R_7$ groups are methyl.

The preparation of the copolymer having the above described components can be performed in accordance with processes known in the art, from starting materials which are either commercially available or can be made in accordance with well known processes.

The elastomeric silicone composition preferably contains a reinforcer, for example, a fume silica reinforcer, such as trimethylsilyl treated silica reinforcer, finely dispersed therein.

The reinforcer, for example, the fume silica reinforcer, is preferably used in an amount of about 15 to about 45 parts by weight of the reinforcer to 100 parts of the copolymer. Fume silica itself is commercially available. The fume silica reinforcer preferably used has a surface area of about 100 to about 450 meter$^2$/gram. More preferably, the fume silica has a surface area of about 200 meter$^2$/gram, is present in an amount (by weight) of about 27 parts (by weight) to 100 parts (by weight) of the copolymer, and is trimethylsilylated with hexamethyldisilazane substantially in the same step where the copolymer is intimately mixed with the silica.

The intimate mixture of the fume silica with the copolymer is commonly termed the "base" in the art. For the purpose of making materials suitable for intraocular lens, the base may be dispersed in a suitable inert solvent, such as trichlorotri- fluoroethane, and the dispersion filtered to remove any solid impurities. Thereafter, the solvent is removed by gentle heat and vacuum.

In accordance with standard practice in the art, the base is divided into two aliquots which preferably are of equal weight. The aliquots are commonly termed "Part A" and "Part B".

Silicon bonded hydride groups are added to the second aliquot (Part B) in the form of cross-linking agents, which are conventional and well known in the art. The liquid organohydrogen polysiloxane cross linkers having the formula $(R)_a (H)_b SiO_{4-a-b/2}$ wherein R is simple lower alkyl, for example, methyl, and a ranges from about 1.00 to about 2.10 and b ranges from about 0.1 to about 1.0, are eminently suitable.

The platinum catalyst can be selected from materials which are conventional and well known in the art.

The cross-linking should not proceed too rapidly at room temperature, thereby allowing at least two, preferably about six hours for work time with the mixed aliquots. For this reason, a suitable cross-linking inhibitor, such as 1, 2, 3, 4 tetramethyl- 1, 2, 3, 4-tetravinyl cyclotetrasiloxane, may be added to the second aliquot (Part B).

Formation of intraocular lens bodies may be accomplished by liquid injection molding, or by cast or compression molding of the intimately mixed Parts A and B.

Although an exemplary embodiment of the invention has been shown and described, many changes, modifications, and substitutions may be made by those having ordinary skill in the art without departing from the spirit and scope of this invention.

What is claimed:

1. An intraocular lens for implantation in an eye comprising:

an optic including an optical zone of desired optical power and having an optical axis and a periphery, and a peripheral zone directly adjacent and circumscribing said optical zone and having reduced optical power relative to said optical zone, said peripheral zone having an axial thickness directly adjacent said periphery of said optical zone which is larger than the axial thickness of said periphery of said optical zone, said optic being configured so that said optic can be resiliently folded or rolled from a normal optical condition into an insertion condition to permit said intraocular lens to be passed through an incision into the eye; and one or more fixation members directly attached to said optic and extending outwardly away from said optic for retaining said optic in the eye, provided that said optical zone is free of said one or more fixation members.

2. The intraocular lens of claim 1 wherein said periphery of said optical zone has a substantially uniform thickness.

3. The intraocular lens of claim 1 wherein said one or more fixation members has a proximal end portion which extends in a direction generally tangential to said optic.

4. The intraocular lens of claim 1 wherein said optical zone is constructed of optically clear material and said peripheral zone is structured to provide reduced glare.

5. The intraocular lens of claim 1 wherein said peripheral zone is at least partially roughened.

6. The intraocular lens of claim 1 wherein said optical zone and said peripheral zone are made of the same material.

7. The intraocular lens of claim 1 wherein said optic is constructed of a silicone based material.

8. The intraocular lens of claim 1 wherein said optical zone has at least about 20 diopter power, and said optic has a maximum cross sectional area of no greater than about 5.8 square millimeters, and said optical zone has an index of refraction of at least about 1.40.

9. The intraocular lens of claim 8 wherein said optical zone has a thickness along said optical axis of no less than about 0.65 millimeters, and the maximum thickness of said peripheral zone in the axial direction is no less than about 0.305 mm.

10. The intraocular lens of claim 1 wherein said insertion condition is such as to permit said intraocular lens to be passed through a scleral tunnel incision having a dimension of no larger than about 3.0 millimeters.

11. An intraocular lens for implantation in an eye comprising:

an optic configured so that said optic can be resiliently folded or rolled from a normal optical condition into an insertion condition to permit said intraocular lens to be passed through an incision into the eye, said optic including an optical zone of desired optical power and having a periphery, and a peripheral zone directly adjacent and circumscribing said optical zone and having reduced optical power relative to said optical zone, said peripheral zone having an axial thickness directly adjacent said periphery of said optical zone which is larger than the axial thickness of said periphery of said optical zone; and one or more fixation members directly attached to said peripheral zone and extending outwardly away from said peripheral zone, provided that said optical zone is free of said one or more fixation members.

12. The intraocular lens of claim 11 wherein said peripheral zone has substantially no effective optical power.

13. The intraocular lens of claim 11 wherein said insertion condition is such as to permit said intraocular lens to be passed through a scleral tunnel incision having a dimension of no larger than about 2.8 millimeters.

14. The intraocular lens of claim 11 wherein said insertion condition is such as to permit said intraocular lens to be passed through a scleral tunnel incision having a dimension of no larger than about 3.0 millimeters.

15. The intraocular lens as of claim 11 wherein said one or more fixation members each comprises a filament having a proximal end portion which extends in a direction generally tangential to said optic.

16. The intraocular lens of claim 11 wherein said optical zone is constructed of optically clear material and said peripheral zone is structured to provide reduced glare.

17. The intraocular lens of claim 11 wherein said peripheral zone is at least partially roughened.

18. The intraocular lens of claim 11 wherein said optical zone has at least about 20 diopter power, and said optic has a maximum cross sectional area of no greater than about 5.8 square millimeters, and said optical zone has index of refraction of at least about 1.40.

19. The intraocular lens of claim 11 wherein said optic is constructed of a silicone based material.

20. An intraocular lens for implantation in an eye comprising:

an optic including an optical zone of desired optical power and having an optical axis and a periphery, and a peripheral zone directly adjacent and circumscribing said optical zone and having reduced optical power relative to said optical zone, said peripheral zone having an axial thickness directly adjacent said periphery of said optical zone which is larger than the axial thickness of said periphery of said optical zone, said optic being configured so that said optic can be resiliently deformed from a normal optical condition into a deformed insertion condition to permit said intraocular lens to be passed through an incision into the eye, said deformed insertion condition being such as to permit said intraocular lens to be passed through a scleral tunnel incision having a dimension of one larger than about 3.0 millimeters; and one or more fixation members coupled to said peripheral zone and extending outwardly away from said peripheral zone for retaining said optic in the eye.

21. An intraocular lens for implantation in an eye comprising:

an optic including an optical zone of desired optical power and having an optical axis and a periphery, and a peripheral zone directly adjacent and circumscribing said optical zone and having reduced optical power relative to said optical zone, said peripheral zone having an axial thickness directly adjacent said periphery of said optical zone which is larger than the axial thickness of the periphery of said optical zone, said optic being configured so that said optic can be resiliently folded or rolled from a normal optical condition into an insertion condition to permit said intraocular lens to be passed through a small incision into the eye; and one or more fixation members coupled to said optic and extending outwardly away from said optic for retaining said optic in the eye, each of said one or more fixation members including a proximal end portion which is located in said optic and extends in a direction generally tangential to said optic, provided that said optical zone is free of said one or more fixation members.

22. An intraocular lens for implantation in an eye comprising:

an optic configured so that said optic can be resiliently deformed from a normal optical condition into a deformed insertion condition to permit said intraocular lens to be passed through an incision into the eye, said optic including an optical zone of desired optical power and having a periphery and a peripheral zone directly adjacent and circumscribing said optic and having reduced optical power relative to said optical zone and an axial thickness directly adjacent said periphery of said optical zone which is larger than the axial thickness of said periphery of said optical zone, said deformed insertion condition being such as to permit said intraocular lens to be passed through a scleral tunnel incision having a dimension of no larger than about 3.2 millimeters; and one or more fixation members coupled to said peripheral zone and extending Outwardly away from said peripheral zone, provided that said optical zone is free of said one or more fixation members.

23. The intraocular lens of claim 22 wherein said deformed insertion condition is such as to permit said intraocular lens to be passed through a scleral tunnel incision having a dimension of no larger than about 3.0 millimeters.

24. An intraocular lens for implantation in an eye comprising:

an optic configured so that said optic can be resiliently deformed from a normal optical condition into a deformed insertion condition to permit said intraocular lens to be passed through a scleral tunnel incision having a dimension of no larger than about 3.2 millimeters, said optic including an optical zone of desired optical power and having a periphery and a peripheral zone directly adjacent and circumscribing said optical zone, said peripheral zone having an axial thickness directly adjacent said periphery of said optical zone which is larger than the axial thickness of said periphery of said optical zone and having reduced optical power relative to said optical zone; and one or more fixation members coupled to said peripheral zone and extending outwardly away from said peripheral zone, provided that said optical zone is free of said one or more fixation members, and said one or more fixation members each comprises a filament having a proximal end portion which is located in said peripheral zone and extends in a direction generally tangential to said optic.

* * * * *